United States Patent
Safo et al.

(10) Patent No.: US 9,765,017 B2
(45) Date of Patent: Sep. 19, 2017

(54) ALLOSTERIC HEMOGLOBIN MODIFIERS WITH NITRIC OXIDE RELEASING MOIETY

(71) Applicant: VIRGINIA COMMONWEALTH UNIVERSITY, Richmond, VA (US)

(72) Inventors: Martin K. Safo, Richmond, VA (US); Richmond Danso-Danquah, Richmond, VA (US); Mohini Ghatge, Richmond, VA (US); Jurgen Venitz, Richmond, VA (US); Martin Mangino, Richmond, VA (US); Kevin R. Ward, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 15/107,962

(22) PCT Filed: Dec. 22, 2014

(86) PCT No.: PCT/US2014/071888
§ 371 (c)(1),
(2) Date: Jun. 24, 2016

(87) PCT Pub. No.: WO2015/100235
PCT Pub. Date: Jul. 2, 2015

(65) Prior Publication Data
US 2016/0326097 A1    Nov. 10, 2016

Related U.S. Application Data

(60) Provisional application No. 61/921,204, filed on Dec. 27, 2013.

(51) Int. Cl.
*C07C 235/38* (2006.01)
*A61K 31/655* (2006.01)
*C07C 245/24* (2006.01)
*A61K 31/216* (2006.01)
*A61K 31/40* (2006.01)
(Continued)

(52) U.S. Cl.
CPC .......... *C07C 235/38* (2013.01); *A61K 31/216* (2013.01); *A61K 31/40* (2013.01); *A61K 31/655* (2013.01); *A61K 33/00* (2013.01); *A61K 45/06* (2013.01); *C07C 245/24* (2013.01)

(58) Field of Classification Search
None
See application file for complete search history.

(56) References Cited

U.S. PATENT DOCUMENTS

| 5,432,191 | A | 7/1995 | Abraham et al. |
| 2005/0154062 | A1 | 7/2005 | Abraham et al. |
| 2007/0293698 | A1* | 12/2007 | Quick .................. A61K 31/195 562/455 |

FOREIGN PATENT DOCUMENTS

| WO | 97/34594 A2 | 9/1997 |
| WO | 2012/075244 A2 | 6/2012 |

* cited by examiner

*Primary Examiner* — Anna Pagonakis
(74) *Attorney, Agent, or Firm* — Whitham, Curtis & Cook, P.C.

(57) ABSTRACT

Allosteric hemoglobin (Hb) modifiers of hemoglobin which contain nitric oxide (NO) moieties allowing for the release of NO in vivo. The compounds retain the oxygen delivery capability of the allosteric hemoglobin modifier to bind Hb and enhance Hb's ability to deliver oxygen to cells and tissues, and also release NO from the NO moiety. Methods of delivering oxygen and/or NO to cells and tissues are also provided.

9 Claims, 4 Drawing Sheets

(51) Int. Cl.
*A61K 33/00* (2006.01)
*A61K 45/06* (2006.01)

ALLOSTERIC HEMOGLOBIN MODIFIERS WITH NITRIC OXIDE RELEASING MOIETY

BACKGROUND OF THE INVENTION

Field of the Invention

Embodiments described herein generally relate to, but are not limited to, novel nitric oxide (NO)-releasing allosteric hemoglobin (Hb) modifiers, as well as compositions containing the same and methods of using the same for the treatment of humans and animals. In some embodiments, the compounds can be administered to a subject to increase tissue oxygenation, as well as to utilize several NO-associated pharmacologic properties, including vasodilatory, anti-inflammatory and anti-oxidant properties.

Background of the Invention

Hemoglobin (Hb) exists in equilibrium between two alternative states, the tense or T state (unliganded or deoxygenated Hb), which possesses low oxygen affinity, and the relaxed or R state (liganded or oxygenated Hb), which has a high oxygen affinity. The tetrameric Hb structures are composed of two $\alpha\beta$ dimers; arranged around a 2-fold axis of symmetry, resulting in a large central water cavity in the structures. The allosteric equilibrium of Hb can be modulated by effectors. A shift toward the relaxed state left-shifts the oxygen equilibrium curve (OEC), producing a high affinity Hb that more readily binds and holds oxygen. A shift toward the T state (right-shift) produces a low affinity Hb that readily releases oxygen. For instance, preferential binding of the endogenous Hb allosteric effector, 2,3-diphosphoglycerate (2,3-DPG) at the central water cavity in the T state leads to additional stabilization of the T state form relative to the R state, further decreasing the affinity of T state Hb for oxygen, causing release of more $O_2$ from the Hb, and thus increasing tissue oxygenation.[1] The degree of shift in the OEC is reported as an increase or decrease in $P_{50}$ (oxygen tension at 50% Hb $O_2$ saturation). The degree of allosteric character/cooperativity demonstrated by Hb is described by the Hill coefficient (n).

Only about 25% of the oxygen bound to Hb is released to tissues at physiological partial pressure of oxygen (pO2). Therefore, any disease states that decrease blood flow, such as vessel narrowing or weakening of heart pumping capacity, reduces the amount of oxygen delivered to the tissues. Blood flow reduction can only be compensated marginally by increased O2-release.

Efaproxiral or RSR-13, (2-[4[[(3,5-dimethylanilino)carbon]methyl]phenoxyl]-2-methylpropionic acid) is a very potent synthetic allosteric effector of Hb, inducing the protein to exhibit low oxygen affinity and very low cooperativity by allosterically stabilizing the deoxygenated Hb.[2-5] RSR-13, the lead synthetic allosteric hemoglobin modifiers (SAM) and its analogs are known to bind to Hb and decrease its affinity for oxygen by increasing the $P_{50}$ (partial pressure of oxygen at which 50% of Hb is saturated with oxygen) of native hemoglobin, i.e. shifting the oxygen equilibrium curve to the right (U.S. Pat. No. 5,432,191). This property allows enhancement of oxygen delivery to ischemic and hypoxic tissues[26], potentially useful for the treatment of various forms of shock, stroke, myocardial ischemia[6], cerebral traumas, angina; radiosensitization of tumors[7-9]; treatment of disorders related to low oxygen delivery to the brain, such as Alzheimer's, depression, and Schizophrenia; in preparing blood substitutes; shelf-life prolongation of stored blood; reduction of surgical blood loss and blood transfusions. The synthesis of RSR-13 and related right shifting allosteric hemoglobin modifiers as well as there use in a myriad of medical applications are described in U.S. Pat. Nos. 5,122,539; 5,290,803; 5,432,191; 5,525,630; and 5,677,330, each of which are herein incorporated by reference.

RSR-13 has also been shown to have direct potent anti-tumor effect by inhibiting tumor growth and their eventual eradication as a result of the inhibition of angiogenesis following an increased oxygen delivery. The ability to increase oxygen delivery to tissue also makes RSR-13 and its analogs potentially useful for increasing physical performance during oxygen deprivation (examples include, but are not limited to, high altitude environments, aquatic environments, and illnesses involving a decrease in lung capacity).

RSR-13 has also been proposed as a means to treat carbon monoxide (CO) poisoning by off-loading CO from hemoglobin through the shift in $P_{50}$ similar to that of off-loading oxygen. This is described in U.S. Pat. No. 5,525,630, where the use of RSR-13 to clear CO bound to Hb in rats exposed to sub-lethal, circulating COHb level of approximately 40% was shown.

Finally, RSR-13 has been proposed to enhance the bioavailability of CO, NO and other gases and to reduce binding of other therapeutic gases that may bind with native hemoglobin, hemoglobin-based oxygen carriers (HBOCs), or other metalloproteins and chromophores that have gas carrying potential (US Patent application 2013/0266668, which is herein incorporated by reference).

NO is endogenously produced in the vascular endothelium or red blood cells (RBC) by nitric oxide synthase and is an important signaling molecule involved in many physiological processes, most notably activating soluble guanylyl cyclase in smooth muscle to induce vasodilation.[10-14] In addition to its vasodilatory properties, NO also modulates inflammation, inhibits vascular remodeling, and affects the multi-step cascade of events involved in leukocyte, platelet and endothelial activation. NO has also been suggested to function as an antioxidant, involved in detoxifying high oxidation states of Hb under oxidative conditions. NO has also been shown to lead to increased oxygen delivery and erythrocyte mobility in ischemic tissue. As a result of NOs vasodilatory, anti-inflammatory and anti-oxidant properties, there has been great interest in developing the means to exogenously deliver NO for therapeutic purposes or to enhance its endogenous production.

Strategies to enhance delivery of NO to tissues have included inhalation of NO, use of medications to increase NO concentrations or to increase production by the body, and mechanical methods of increasing shear stress at the vascular level to promote production of NO. The use of inhaled NO has been used to treat pulmonary hypertension and other diseases such as sepsis.[15-21] For example, inhaled NO has been tested for the treatment of tissue damage in various ischemic related diseases, such as cardiovascular disease, pulmonary arterial hypertension, and acute lung distress syndromes damages. NO donating compounds have also been studied for a long time on account of the pharmacological properties of the NO released. However, there are limitations to dosing of exogenous NO. NO has a very short half-life and when it is present in plasma, it is believed to be rapidly sequestered by Hb and inactivated and thus is not available to exert is beneficial effects.

It is also important to note that binding of NO to hemoglobin is of even bigger concern with the use of hemoglobin based oxygen carriers (HBOCs). Hb functions by binding and transporting oxygen from the lungs to the tissues, and offloading to respiring cells. Due to several problems associated with blood transfusion, cell-free HBOCs have been under investigation for several decades for potential use to support blood oxygen transport during hemorrhage shock, sepsis, hemolysis and various ischemic insults ranging from stroke to myocardial infarction, to traumatic brain and spinal cord injury, among others. HBOCs have thus been developed as a means to deliver oxygen to tissues as an alternative to native human blood. In general, these agents are made by taking human or bovine hemoglobin out of red blood cells and processing it in a way that produces linked tetramers and other configurations of Hb. These can be further modified if desired through either re-encapsulation in an artificial membrane or through processes such as PEGylation in order to increase the circulating half-life of the HBOC. Although, these blood substitutes have demonstrated efficacy in both animal models and humans, several serious safety problems, including death, have impeded their clinical use.[22-23] For example, a characteristic and persistent side effect of many of these HBOCs has been the propensity to cause vasoconstriction and increase blood pressure due to the scavenging of endogenously produced NO.[24]

A general side effect in the processing and production of HBOCs is that they become potent scavengers of NO[25] and as a result can cause undesired increases in blood pressure during their use to treat hemorrhage, which may paradoxically result in more hemorrhage. This has resulted, in part, in no HBOC being approved by the FDA due to concerns that their use causes increased bleeding. Hemorrhage from many causes results in increased production of endogenous NO, as the body's way of attempting to lessen bleeding by relaxing blood vessels and maintaining microcirculatory blood flow and tissue oxygenation. Unfortunately, the potential benefits of administering HBOCs in order to treat hemorrhage (e.g. to replace lost blood and/or increase oxygen delivery to tissue), are nullified or at least lessened when the HBOCs scavenge NO, causing an increase in blood pressure and thus additional hemorrhage. In addition, this scavenging may reduce microvascular blood flow thus worsening tissue perfusion and oxygenation. Other complications have included a higher than expected incidence of myocardial damage which may be due to enhanced binding of NO by HBOCs.

Another potentially unwanted side effect of HBOCs is that the $P_{50}$ of the resulting HBOC is sometimes significantly reduced. This has the effect of decreasing the ability of the HBOC to release oxygen in the setting for which it is designed. While several manufacturers claim a low $P_{50}$ is an advantage, replacement of significant amounts of native hemoglobin with an HBOC of low $P_{50}$ ultimately results in tissue hypoxia. While the ability of an HBOC to tightly bind and carry large amounts of $O_2$ might appear to be advantageous, if the $O_2$ is not expeditiously released to the tissues during circulation, then the purpose of the increased $O_2$ binding capacity is defeated.

In summary, exogenous NO, either through inhalation or via use of hemoglobin-based oxygen carriers (HBOCs) has been shown to have therapeutic value, including anti-inflammation, vasodilation or tissue protection. The key to its effectiveness is enhancing its bioavailability in plasma so that they are free to interact with the vasculature and with the organ and immune cells of the body to exert their beneficial effects. Thus, means to reduce their binding to either native hemoglobin or the hemoglobin of HBOCS are needed to optimize their bioavailability and to reduce their cytotoxic effects. While the use of acellular non-HBOC gas carriers such as intravenous perfluorocarbons (PFCs) can increase the solubility of and concentration of exogenously administered NO and $O_2$ in plasma, this enhanced concentration will not reduce the binding of these gases to hemoglobins, native or otherwise. Thus, in the absence of a solution to the sequestration of NO by native Hb and HBOCs, and the untoward side effects caused by this sequestration, the increased concentrations caused by PFCs are not helpful.

There is a need for the development of NO-releasing Hb modifiers that reduce Hb NO binding thus making NO more bioavailable to tissues while maintaining the ability to decrease Hbs affinity for $O_2$ thereby enhancing $O_2$ delivery to tissues.

SUMMARY OF THE INVENTION

Embodiments of the invention provide a novel group of hybrid NO-releasing right-shifting allosteric Hb modifiers. In particular, a NO releasing moiety is incorporated into RSR-13 or its analogs as organic nitrate, diazenuim diolate esters, etc. In addition to their ability to increase tissue oxygenation, these compounds also have several NO-associated pharmacologic properties, including vasodilatory, anti-inflammatory and anti-oxidant properties. Some embodiments of the invention also provide therapeutic methods i) to enhance the bioavailability of at least one of NO and $O_2$; and ii) to improve the efficacy of HBOCs with respect to delivery of oxygen to cells and tissues and to mitigate side effects.

The NO-releasing allosteric Hb modifiers described herein have applications in cardiovascular diseases, acute ischemic diseases, and inflammatory diseases. These compounds have vasodilatory, anti-inflammatory, and anti-oxidant properties and can also increase erythrocyte mobility. These allosteric effectors of Hb act like a prodrug in that they release NO in vivo while retaining the ability of the RSR-13 compound or RSR-13 like compound (an RSR-13 analog) to bind Hb and decrease it affinity for $O_2$ thereby enhancing the ability of Hb to deliver $O_2$ to tissues (i.e. right shifting the $O_2$ equilibrium curve).

In some embodiments, the allosteric effectors described herein are co-administered with at least one HBOC. As described above, the allosteric modulator or effector increases the $P_{50}$ of Hb. Without being bound by theory, it appears that such allosteric modifiers also exert similar effects on HBOCs. In other words, the allosteric agents appear to also cause an increase in $P_{50}$ of the HBOC, resulting in more $O_2$ being released from the HBOC and delivered to cells and tissues of a subject, thereby preventing or overcoming the limitations and untoward side effects of HBOC administration according to hitherto known methods. The effector appears to cause a shift in the equilibrium distribution of bound vs free gas, in favor of free, bioavailable gas. In addition, co-administration of an HBOC and such an effector also increases the ability of the HBOC to release other medicinal gases (e.g. NO, $O_2$, nitrogen dioxide ($N_2O$), CO, hydrogen sulfide ($H_2S$), sulfur monoxide (SO), sulfur dioxide ($SO_2$), etc.), and in some embodiments of the method, medicinal gases are co-administered with the HBOC. This latter point is particularly important in regards to NO where its binding with HBOCs have resulted in complications. The same holds true for mixtures of e.g. erythrocyte Hb and HBOCs.

Embodiments of the invention provide methods of using allosteric modifiers which increase the $P_{50}$ of Hb or HBOC in at least the following exemplary applications:

1) Enhance the bioavailability of endogenously produced NO and $O_2$ either alone or in combination, by reducing their binding to native hemoglobin for therapeutic purposes.
2) Enhance the bioavailability of NO or exogenously administered CO, NO, $H_2S$, $O_2$, and other medicinal gases released from HBOCs either alone or in combination, for therapeutic purposes.
3) Enhance the therapeutic efficacy of HBOCs by reducing their propensity to bind NO, $H_2S$, CO, and other medicinal gases.
4) Enhance the therapeutic efficacy of HBOCs by increasing their $P_{50}$ to enhance the off-loading of oxygen.

DETAILED DESCRIPTION

Figure 1:
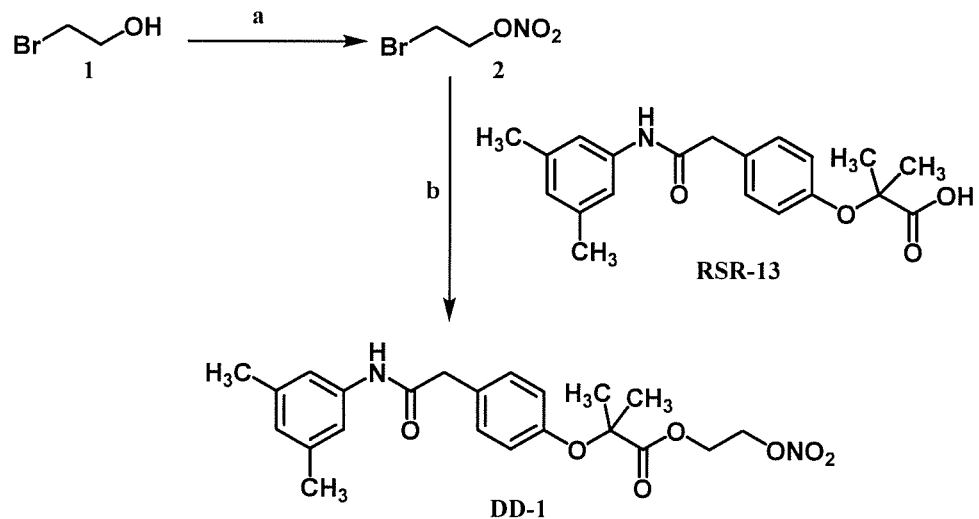
FIG. 1. Synthesis scheme of DD-1 (2-(Nitrooxy)ethyl 2-(4-(2-((3,5-dimethylphenyl)amino)-2-oxoethyl)phenoxy)-2-methylpropanoate). Reagent: (a) $H_2SO_4$, $HNO_3$, anhydrous $CH_2Cl_2$ (b) $K_2CO_3$, anhydrous DMF FIG. 2. Synthesis scheme of DD-2 (2-(Nitrooxy)propyl 2-(4-(2-((3,5-dimethylphenyl)amino)-2-oxoethyl)phenoxy)-2-methylpropanoate). Reagent: (a) $H_2SO_4$, $HNO_3$, anhydrous $CH_2Cl_2$ (b) $K_2CO_3$, anhydrous DMF FIG. 3. Synthesis scheme of compound DD-3 ((Z)-1-((2-(4-(2-((3,5-dimethylphenyl)amino)-2-oxoethyl)phenoxy)-2-methylpropanoyl)-peroxy)-3,3-diethyltriaz-1-ene 2-oxide). Reagent: (a) Nitric oxide, $CH_3ONa$, anhydrous diethyl ether (b) $K_2CO_3$, $ClCH_2SCH_3$, HMPA, (c) $SO_2Cl$, $CH_2Cl_2$ FIG. 4. Time dependent OEC studies of DD-1 and RSR-13 showing changes in $P_{50}$ with incubation time.

It is an object of the invention to provide an allosteric effector of hemoglobin (Hb) having the general formula of formula I:

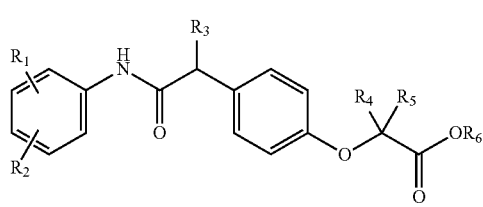

Formula I wherein
R1 and R2 are the same or different and are $CH_3$, Cl, H, $OCH_3$, or 5-carbon cyclic incorporating both R1 and R2;
R3 is H, OH, COOH, or $OC_2H_5$;
R4 and R5 are the same or different and are H, $CH_3$, cyclic incorporating both R4 and R5 and containing $CH_3$ substituents, $OCH_3$, $C_2H_5$, phenyl, or unsubstituted phenyl; and R6 is a NO containing moiety. Examples of some NO containing moieties which may be used in the practice of the invention are shown below

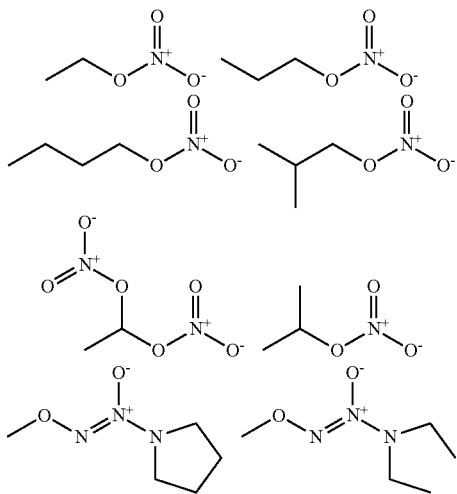

and the NO containing moiety of R6 includes functional variants, analogues, isomers and salts thereof.

In some embodiments, the effector is compound DD-1 (2-(Nitrooxy)ethyl 2-(4-(2-((3,5-dimethylphenyl)amino)-2-oxoethyl)phenoxy)-2-methylpropanoate) or DD-2 (2-(Nitrooxy)propyl 2-(4-(2-((3,5-dimethylphenyl)amino)-2-oxoethyl)phenoxy)-2-methylpropanoate) or DD-3 ((Z)-1-((2-(4-(2-((3,5-dimethylphenyl)amino)-2-oxoethyl)phenoxy)-2-methylpropanoyl)-peroxy)-3,3-diethyltriaz-1-ene 2-oxide).

Exemplary compounds of the invention are derivatives of "RSR-13". RSR-13 is also known by its International Nonproprietary Name (INN) "efaproxiral" and its IUPAC designation is 2-[4-[2-[(3,5-dimethylphenyl)amino]-2-oxoethyl]phenoxy]-2-methylpropanoic acid). RSR-13 is a compound within the family defined by the general formula of formula I, wherein R6 is a hydrogen. Compounds of this type and variants and analogues thereof are described in U.S. Pat. Nos. 5,122,539; 5,248,785; 5,250,701; 5,290,803; 5,525,630; 5,591,892; 5,648,375; 5,661,182; 5,677,330; 5,705,521; 5,731,454; 5,827,888; 5,872,282; and 5,927,283, the complete contents of each of which are hereby incorporated by reference.

Embodiments of the invention also include compositions comprising one or more allosteric effectors of Hb as described herein and a carrier. The carrier may be a pharmaceutically acceptable solid or liquid or gas (e.g., air). In the case of a liquid carrier, the one or more allosteric effectors of Hb are dissolved or distributed in the carrier.

In some embodiments, the invention provides a method of delivering $O_2$ and/or NO to cells and tissues of a subject in need thereof. This is accomplished by administering to the subject an allosteric effector of Hb as described herein, or a composition containing one or more of the allosteric effectors, by a suitable administration route (e.g., oral, perenteral (i.p., i.v., i.m., subcutaneas, topical, etc.).

In some embodiments, at least one hemoglobin based oxygen carrier (HBOC) is co-administered with an allosteric effector as described herein. In some embodiments, the method further comprises the step of providing to said patient at least one medicinal gas, wherein the step of providing can be carried out by exogenous administration. In some embodiments, the step of providing includes a step of applying to said subject at least one exogenous stimulus which elicits endogenous production of the at least one medicinal gas. The medicinal gas may be selected from NO, CO, $H_2S$, $N_2O$, SO, $SO_2$ and $O_2$.

The invention also provides methods of treating poisoning by gases such as CO, $H_2S$ and $NO_2$. The method involves co-administering to subject or patient in need thereof (i.e. one suffering from gas poisoning) i) an allosteric modulator of Hb as described herein, alone or in combination with ii) one or both of an HBOC and a PFC. As a result of administering the agent (the allosteric modifiers of hemoglobin described herein), native hemoglobin and, if present, the HBOC, release more $O_2$ into circulation, while the agent also prevents the poisoning gas from binding to Hb and/or the HBOC. As a result, more oxygen is delivered to tissues and more poisonous gas is flushed from the system.

The compounds of the invention beneficially affect patients by reducing inflammation, increasing tissue perfusion, decreasing blood pressure, and acting as an antioxidant. The compounds also assist in vasodilating the microvasculature and/or increasing erythrocyte mobility to enhance tissue blood flow and thus oxygen delivery, which is useful for treating ischemic-related diseases, such as myocardial ischemia.

The allosteric effector compounds of the invention change the binding of a gas (e.g. $O_2$) to a gas carrier such as Hb, meaning that the binding affinity of the gas for the carrier in the presence of the compound differs from the binding affinity of the gas for the carrier in the absence of the compound. Generally, the change is a change of at least about 5, 10, 20, 30, 40, 50 60, 70, 80, 90, or 100%, and may be a change of about 1, 2, 3, 4, 5, 6, 7, 8, 9, 10, 20, 30, 40, 50, 60, 70, 80, 90 or 100-fold, or even more (e.g. a 500- or even 1000-fold change). Advantageously, the change is a decrease in binding affinity, which results in a greater release of the gas from the carrier into the surrounding milieu or a decrease in the uptake of the gas (e.g. a deleterious or poisonous gas) from the surrounding milieu to Hb as a gas carrier.

"$P_{50}$" refers to the partial pressure of a gas such as oxygen at which a gas carrier (e.g. an oxygen carrier such as Hb or an HBOC, or a mixture of these) is 50% saturated with the gas. Thus, lower values indicate greater affinity for the gas, i.e. a decreased tendency to release the gas, or, conversely, an increased tendency to retain bound gas. On the other hand, an increase in $P_{50}$, as may be caused by the agents employed as described herein, results in an increased tendency of the carrier to release the gas, or conversely, a decreased tendency to retain bound gas e.g. oxygen.

By "exogenous" administration, we mean a type of administration which includes but is not limited to, for example, intravenous, dermal and oral administration, inhalation, etc.

By "endogenous" administration, we mean that the gas is technically produced by the body, for example, in response to inadvertent trauma. Alternatively, the "endogenous" production of the gas may be purposefully induced, e.g. by the deliberate application of an exogenous stimulus or means such as mechanically through a cuff or tourniquet which causes ischemia and/or reperfusion, or by mechanical means such as vibrating, or by providing precursors to the gas intravenously, etc.

The "bioavailability" of a therapeutic gas as used herein refers to the degree to which or rate at which a therapeutic agent such as a medicinal gas is absorbed and/or becomes available at the site of physiological activity to exert its effect.

By co-administration or administered together, we mean that two (or more) agents are administered so as to both (or all) be present in a subject at the same time, or at least at overlapping times, or at least so that the effect of each agent is still present in the subject when the other(s) are administered. The agents may literally be administered at the same time (either in a single composition, or in separate compositions), or sequentially within a relatively short period of time, or one may be administered more or less continuously and the other(s) administered during the time of administration, or one or more of the agents may be in a sustained, long acting formulation, etc.

Examples of medicinal gases that may be administered according to the methods of the invention include, but are not limited to, NO, CO, $H_2S$, $N_2O$, SO, $SO_2$ and $O_2$. An administrable source of a medicinal gas may be, for example: medical grade NO and CO are available for direct inhalation and can be mixed with oxygen; a PFC that is loaded with one or more gases of interest may be administered; CO-releasing molecules (CORMs) such as [Mo(CO)$_3$(histidinato)]Na are water soluble and when injected release CO; compounds that break down and release e.g. $H_2S$ or another medicinal gas in an aqueous environment such as in blood or plasma in vivo, etc. may be used; injection of NaHS intravenously produces $H_2S$ as is described in a review by Czabo;[27] injection of NO donors such as nitrates and Naproxen-NO will subsequently increase circulating levels of NO as described in a review by Thatcher and colleagues.[28]

HBOCs that can be used in the practice of the invention include but are not limited to: HBOC-1, and functional variants thereof, as well as those which are described in the following: U.S. Pat. No. 4,001,401 to Bonson et al., and U.S. Pat. No. 4,061,736 to Morris et al., the complete contents of each of which are herein incorporated by reference, describe different approaches to producing viable blood substitutes which may be used in the practice of the present invention. U.S. Pat. Nos. 7,803,912; 7,642,233; 7,307,150; 7,005,414; 6,894,150; 6,812,328; 6,808,898; 6,803,212; 6,506,725; 6,486,123; 6,172,039; 6,083,909; 6,072,072; 6,005,078; 5,962,651; 5,955,581; 5,674,528; and 5,661,124, among others, describe various HBOCs and/or methods of making HBOCs that are suitable for use in the present invention, as do US patent applications 20100323029; 20080305178; 20070172924; 20050113289; 20040029780; 20030181358; among others, and the complete contents of each of these patents and patent application are herein incorporated by reference in entirety. Any HBOC, the $P_{50}$ of which can be increased by a modifying agent such as an allosteric modifying agent, may be used in the practice of the invention. The complete contents of each of the foregoing patents and patent applications are hereby incorporated by reference in entirety.

The allosteric hemoglobin modifier compounds of the present invention, alone or in combination with the HBOCs, are administered as compositions which are suitable to their properties (i.e. to maintain functionality) and to the desired mode of administration and action. The compositions generally include a pharmacologically suitable carrier. The carrier may be a solid, liquid (e.g., an oil or aqueous liquid), or gas (e.g., air, propellant (hydrofluorocarbon, chlorofluorohydrocarbon, etc.). The preparation of such compositions is well known to those of skill in the art. Typically, such compositions are prepared either as liquid solutions or suspensions, or as solid forms such as tablets, pills, powders and the like. Solid forms suitable for solution in, or suspension in, liquids prior to administration may also be prepared, and preparations may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent in the formulations may vary. However, in general, the amount will be from about 1-99%.

The compositions (preparations) may be administered by any of many suitable means which are well known to those of skill in the art, including but not limited to by injection, inhalation, orally, intravaginally, intranasally, by ingestion of a food or probiotic product, topically, as eye drops, via sprays, etc. In preferred embodiments, the mode of administration is by injection. In addition, the compositions may be administered in conjunction with other treatment modalities such as antibiotic agents, and the like.

The amount of the allosteric effector compound (the allosteric hemoglobin modifier compounds described herein) that is administered in some applications is typically in the range of from about 1 mg/kg to about 500 mg/kg, and is preferably from about 25 mg/kg to about 300 mg/kg, or about 50 mg/kg to about 120 mg/kg, or 75 mg/kg to about 100 mg/kg.

In embodiments involving the simultaneous or serial administration of one or more allosteric hemoglobin modifier compounds in combination with one or more HBOCs, the amount of HBOC that is typically administered in the practice of the invention is in the range of from about 100 cc to about 2000 cc, and is preferably from about 250 cc to about 500 cc. If PFCs are concurrently administered, the amount is generally in the range of from about 0.25 cc/kg to about 10 cc/kg, and is preferably from about 2 cc/kg to about 5 cc/kg. These doses represent bolus doses but may be modified and increased to be provided as continuous infusions while maintaining continuous therapeutic concentrations of the above agents to achieve the desired effects. The doses above of course may change as new studies are performed to optimize combinations for the various therapeutic purposes as they relate to specific diseases. It is also recognized that newer formulations may arise which change the volumes of agents provided.

The methods of the invention can be used to treat any patient or subject suffering from or likely to suffer from a disease or condition which can be prevented, treated, cured, or ameliorated (i.e. disease symptoms are reduced or abated compared to not receiving the compounds) by increasing the concentration and/or the bioavailability of a beneficial gas in the circulatory system of the subject. Such patients or subjects are generally mammals, frequently humans, although this need not always be the case.

Veterinary applications of this technology are also encompassed, e.g. to treat companion pets (dogs, cats, etc.), domestic animals such as horses, cattle, goats, sheep, pigs, etc., wildlife in captivity or in preserves (especially rare or endangered species, or those used for breeding purposes), and others that may benefit from the practice of the invention.

Various embodiments or scenarios of use of the methods of the invention include but are not limited to:

1) Patients who have incurred an acute or chronic illness or injury in which the body is producing additional endogenous NO and/or $H_2S$, and/or CO and/or other therapeutic gas (e.g. in order to maintain microvascular blood flow and/or combat inflammation and other cell damaging activities) would be given either a bolus or intermittent, or continuous infusion of an agent such as DD-1 over suitable time periods. The agent acts to release NO through its NO containing moiety. At the same time, tissue oxygenation is concurrently enhanced either with or without the presence of supplemental oxygen. Examples of such chronic or acute illnesses or injuries include but are not limited to: ischemia related diseases, hemorrhagic and traumatic shock, severe infection (bacterial and otherwise), severe sepsis, and septic shock, cardiac arrest and cardiogenic shock, severe burns and wounds, complex surgeries such as transplant surgeries, Crohn's disease, radiation poisoning, traumatic brain injury, stroke, myocardial infarction, vasoocclusive crisis, severe respiratory distress from asthma, chronic obstructive pulmonary diseases, acute respiratory distress syndrome, pulmonary hypertension, preeclampsia, eclampsia, malaria, influenza, organ transplant, coronary heart disease, cerebrovascular disease, hypertension, arthritis, cancer, diabetes and others.

2) Patients who have incurred an acute illness or injury or who have a chronic condition that would benefit from the administration of exogenous NO, $H_2S$ and/or CO or other therapeutic gas with or without supplemental oxygen would have an intravenous bolus or intermittent or continuous infusion of an agent such as DD-1 in conjunction with receipt of the exogenous gases. This embodiment may be further modulated by the concurrent administration of perfluorocarbon emulsions allowing for more NO, CO, $H_2S$, $O_2$ and combinations thereof to be carried by plasma, while still reducing their binding to hemoglobin. In fact, NO, CO, $H_2S$, and/or $O_2$ may be premixed with the PFC to allow their administration intravenously without the need for inhalation of these gases if desired. Examples of such acute illnesses or injuries or chronic conditions include but are not limited to: ischemia related diseases, hemorrhagic and traumatic shock, severe infection (bacterial and otherwise), severe sepsis, and septic shock, cardiac arrest and cardiogenic shock, severe burns and wounds, complex surgeries such as transplant surgeries, Crohn's disease, radiation poisoning, traumatic brain injury, stroke, myocardial infarction, vasoocclusive crisis, severe respiratory distress from asthma, chronic obstructive pulmonary diseases, acute respiratory distress syndrome, pulmonary hypertension, preeclampsia, eclampsia, organ transplant, malaria, influenza, coronary heart disease, cerebrovascular disease, hypertension, arthritis, cancer, diabetes and others.

3) Patients who require supplemental tissue oxygenation with an HBOC would be given an intravenous bolus or intermittent or continuous infusion of an agent such as DD-1 to increase the $P_{50}$ of both the HBOC and native hemoglobin with or without supplemental oxygen, thereby reducing CO, $H_2S$, and NO binding by the HBOC and $O_2$ binding of the native hemoglobin. Examples of illnesses or conditions which can benefit from supplemental tissue oxygenation with an HBOC include but are not limited to: ischemia related diseases, hemorrhagic and traumatic shock, severe infection (bacterial and otherwise), severe sepsis, and septic shock, cardiac arrest and cardiogenic shock, severe burns and wounds, complex surgeries such as transplant surgeries, Crohn's disease, radiation poisoning, traumatic brain injury, stroke, myocardial infarction, vasoocclusive crisis, severe respiratory distress from asthma, chronic obstructive pulmonary diseases, acute respiratory distress syndrome, pulmonary hypertension, preeclampsia, eclampsia, organ transplant, malaria, influenza, coronary heart disease, cerebrovascular disease, hypertension, arthritis, cancer, diabetes and others.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE 1

Synthesis and Characterization of Nitrate Ester Derivatives of RSR-13

Figure 2:
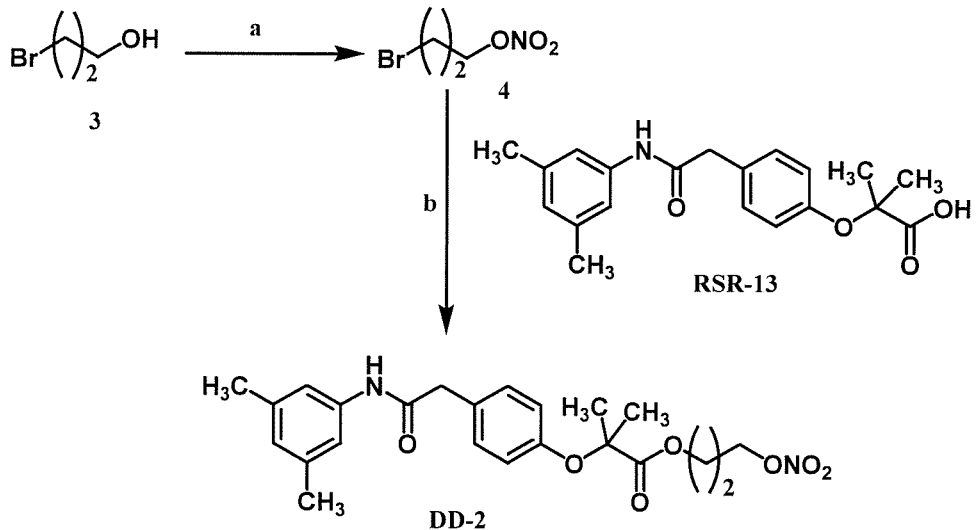
Figure 3:
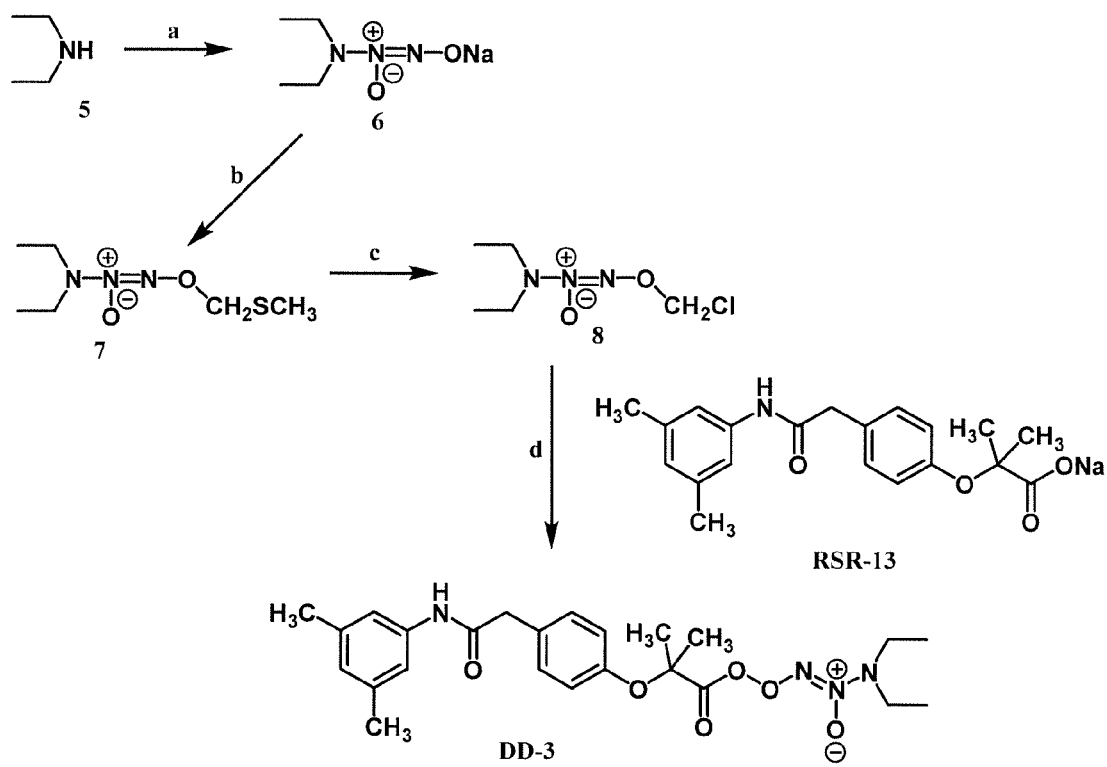

RSR-13 is an allosteric effector of Hb that acts by decreasing Hb affinity for $O_2$, and as a result allows release of more $O_2$ to tissues.[26] In this study, a nitrate ester moiety was incorporated onto RSR-13. It was proposed that, in vivo, the NO will cleave off, resulting in the parent compound and free NO, the former acting as right-shifter of the oxygen equilibrium curve while the latter is released into the vasculature. The following describe the synthesis of three nitrate esters of RSR-13, including DD-1, DD-2 and DD-3 (FIGS. 1-3). Other NO containing RSR-13 derivatives, such as those referenced above may be synthesized according to the same or similar processes. Normal whole blood used in some of the functional assays was collected from adult donors at the Virginia Commonwealth University after informed consent. Hb used for structural studies was purified from discarded normal blood samples. The use of these human samples is in accordance with regulations of the IRB for Protection of Human Subjects.

Synthesis of DD-1 (2-(Nitrooxy)ethyl 2-(4-(2-((3,5-dimethylphenyl)amino)-2-oxoethyl)phenoxy)-2-methylpropanoate) (FIG. 1): To a stirring solution of concentrated sulfuric acid (30 mmol) was slowly added concentrated nitric acid (30 mmol) dropwise at 0° C. under nitrogen. The mixture was stirred for 10 min at the same temperature followed by the addition of 2-bromoethanol 1 (3.1 g, 25 mmol) in anhydrous dichloromethane (5 mL) dropwise while keeping the internal temperature below 5° C. After stirring for 3 h the reaction was quenched with water (10 mL). Dichloromethane (40 mL) added and the organic phase was separated, washed with water (15 mL), dried ($MgSO_4$) and concentrated to give bromoethyl nitrate 2, which was used in the next step without further purification.

RSR-13 (5.8 g, 17 mmol) and potassium carbonate (5.5 g, 40 mmol) were added to a solution of bromoethyl nitrate 2 in anhydrous dimethylformamide (40 mL). The reaction mixture was allowed to stir for 24 h at room temperature, diluted with ethylacetate (150 mL), washed with water (3×40 mL), dried ($MgSO_4$) and evaporated under reduced pressure to give a crude product, and subsequently purified by column chromatography, eluting with petroleum ether/ethylacetate (2:1) to yield 6.3 g of DD-1 as a white solid.

Synthesis of DD-2 (2-(Nitrooxy)propyl 2-(4-(2-((3,5-dimethylphenyl)amino)-2-oxoethyl)phenoxy)-2-methylpropanoate) (FIG. 2): To a stirring solution of concentrated sulfuric acid (30 mmol) was slowly added concentrated nitric acid (30 mmol) dropwise at 0° C. under nitrogen, and stirred for 10 min followed by the addition of 3-bromopropanol 3 (3.5 g, 25 mmol) in anhydrous dichloromethane (5 mL) dropwise while keeping the temperature below 5° C. After 3 h, the reaction was quenched with water (10 mL), followed by addition of dichloromethane (40 mL). The organic phase was separated, washed with water (15 mL), dried (MgSO$_4$) and concentrated to give bromopropyl nitrate 4, which was used in the next step without further purification.

RSR-13 (5.8 g, 17 mmol) and potassium carbonate (5.5 g, 40 mmol) were added to a solution of bromopropyl nitrate 4 in anhydrous dimethylformamide (40 mL). The reaction mixture was allowed to stir for 24 h at room temperature, diluted with ethylacetate (150 mL), washed with water (3×40 mL), dried (MgSO$_4$) and evaporated under reduced pressure to give a crude product, which was then purified by column chromatography, eluting with petroleum ether/ethylacetate (2:1) to yield 5.2 g of DD-2 as a white solid.

Synthesis of DD-3 ((Z)-1-((2-(4-(2-((3,5-dimethylphenyl)amino)-2-oxoethyl)phenoxy)-2-methylpropanoyl)-peroxy)-3,3-diethyltriaz-1-ene 2-oxide) (FIG. 3): Diethylamine 5 (7.3 g, 0.1 mol) was added to a solution of sodium methoxide (0.1 mol, 24 mL of a 25% w/v solution in methanol) and anhydrous diethyl ether (300 mL) with stirring under nitrogen at room temperature. The mixture was then purged with nitrogen for 5 min, and the reaction was allowed to stir under an atmosphere of nitric oxide (40 psi) at room temperature for 5 h. The precipitated product was isolated by filtration, suspended in diethyl ether (100 mL) and stirred for 15 min. The suspension was filtered, and the solid dried at room temperature under pressure to afford 6 (4.0 g). The product was used immediately in the next step after drying without further purification.

The sodium diazeniumdiolate 6 (2.8 g, 18.2 mmol) was added to a suspension of potassium carbonate (0.5 g, 3.7 mmol) and hexamethylphosphoramide (HMPA) (27 mL) at 4° C., and the mixture stirred for 30 min. Chloromethyl methyl sulfide (6.3 g, 21.9 mmol) was added dropwise, and the reaction mixture stirred at room temperature for 72 h. Ethylacetate (70 mL) was added to quench the reaction, and the solid filtered off. The organic phase was washed with water (5×30 mL), dried (MgSO$_4$), and the solvent removed in vacuo to give a crude product which was purified by silica gel column chromatography using ethylacetate/hexane (1:4) as eluent to yield 7 (1.1 g) as a pale yellow liquid and used immediately in the next step.

A solution of compound 7 (1.1 g, 5.7 mmol) in dichloromethane (10 mL) was cooled to 4° C. Sulfuryl chloride (1.15 g, 8.55 mmol, and 8.5 mL of a 1.0 M solution in dichloromethane) was added dropwise, and allowed to stir at the same temperature for 30 min and at room temperature for 8 h. The solvent was removed in vacuo and the residue purified by silica gel column chromatography using ethylacetate/hexane (1:4) as the eluent to furnish 8 (0.7 g) as a yellow oil.

To a stirring solution of sodium salt of RSR-13 (3.63 g, 10 mmol) in HMPA (15 mL) was added a solution of compound 8 (10 mmol) in HMPA (10.0 mL), and the reaction mixture allowed to proceed for 24 h at room temperature. Ethylacetate (30 mL) was added, and the mixture washed with water (5×15 mL). The organic phase was dried (MgSO$_4$), and the solvent removed in vacuo and the product was purified by silica gel column chromatography, eluting with ethylacetate/hexane (1:1) to yield 1.8 g of DD-3.

Effect of DD-1 on Hb Affinity for Oxygen

The effect of DD-1 on Hb affinity for oxygen was studied using whole blood with RSR-13 as a positive control. Solution of DD-1 and RSR-13 was added to 2 mL of whole blood (Hemocrit of ~29%) to make a final drug concentration of 2 mM. Time-dependent studies were carried out at various time points (ranging from 1 h to 12 h) at 37° C. Briefly, blood-drug mixture samples at various time points were incubated in IL 237 tonometer (Instrumentation Laboratories, Inc., Lexington, Mass.) for about 5-7 min at 37° C. against gas mixture containing O$_2$ concentrations of 0.804%, 2.935% and 8.785% and allowed to equilibrate at O$_2$ tensions of 6, 20, 60 mmHg, respectively. After equilibration, the sample was removed via syringe and aspirated into a ABL 700 series table top automated blood gas analyzer (Radiometer America, Inc., Westlake, Ohio) to determine total hemoglobin (tHb), hematocrit (Hct), pH, pCO$_2$, partial pressure of oxygen (pO$_2$), and the Hb oxygen saturation values (sO$_2$). The measured values of pO$_2$ and sO$_2$ at each oxygen saturation level were then subjected to a non-linear regression analysis using the program Scientist (Micromath, Salt Lake City, Utah) with the following equation:

$$sO_2\% = 100 \times \frac{pO_2^N \text{ mmHg}}{P_{50}^N \text{ (mmHg)} (i) + pO_2^N \text{(mmHg)}}$$

This equation was used to calculate P$_{50}$ and Hill coefficient (N) values. Corresponding control experiments without the test compound (P$_{50control}$) but containing DMSO were also performed.

TABLE 1

Effect of DD-1 and RSR-13 on Hb affinity for O$_2$ using normal whole blood.

| Compound | Incubation Time (Hours) | P$_{50}$ (mmHg) | N[a] | ΔP$_{50}$[b] (mmHg) |
| --- | --- | --- | --- | --- |
| Control | 1 | 32.5 | 2.6 | — |
|  | 2 | 32.9 | 2.7 | — |
|  | 4 | 33.6 | 2.6 | — |
|  | 8 | 34.9 | 2.5 | — |
|  | 12 | 37.0 | 2.5 | — |
| RSR-13 | 1 | 47.8 | 1.8 | 15.3 |
|  | 2 | 47.9 | 1.9 | 15.0 |
|  | 4 | 49.7 | 1.8 | 16.1 |
|  | 8 | 51.8 | 1.8 | 16.9 |
|  | 12 | 52.6 | 1.9 | 15.6 |
| DD-1 | 1 | 35.7 | 2.3 | 3.2 |
|  | 2 | 39.2 | 2.1 | 6.3 |
|  | 4 | 49.9 | 1.9 | 16.3 |
|  | 8 | 60.3 | 1.7 | 25.4 |
|  | 12 | 64.8 | 1.7 | 27.8 |

All samples were pre-incubated with whole blood (Hct ~29%) with the specified compounds at 2 mM concentrations for the specified time.
[a]Hill coefficient;
[b]ΔP$_{50}$ is (P$_{50}$ (control) − P$_{50}$ (sample)) expressed in mmHg. The control experiment without test compound (P$_{50}$ (control)) contains the same concentration of DMSO used to solubilize the test solution (P$_{50}$ (sample)).

Figure 4:
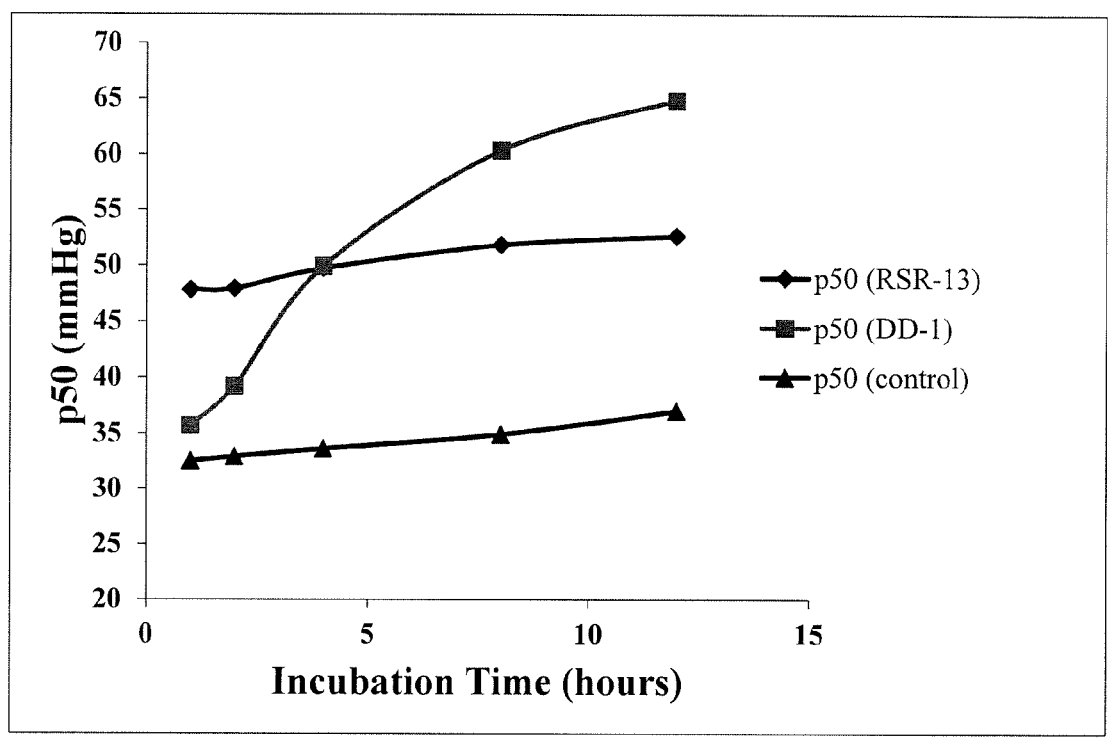

The results showed a gradual increase in the P$_{50}$ values with time, with a maximum P$_{50}$ after 12 h incubation (Table 1). Initially, P$_{50}$ value of DD-1 was lower than that of the parent compound but as the incubation time crossed 4 h, the P$_{50}$ value of DD-1 was seen to increase over the parent compound (Table 1, FIG. 4).

Nitric Oxide Release Study for DD-1

A Griess assay was used to measure the NO releasing ability of DD-1 following literature procedures.[29-31] Solution of the test compound (1 mL of a 2 mM solution in 0.1 M phosphate buffer (pH 7.4)) was mixed thoroughly with a freshly prepared solution of L-cysteine (1 mL of a 36 mM solution in 0.1 M phosphate buffer, pH 7.4), and incubated at 37° C. for 1 and 16 h under anaerobic conditions. After exposure to air for 10 min at 25° C., an aliquot of the Griess reagent (1 mL) [freshly prepared by mixing equal volumes of 1.0% sulfanilamide (prepared and stored in aqueous 5% phosphoric acid) and 0.1% N-naphthylethylenediamine dihydrochloride in water] was added to equal volume (1 mL)

of each incubation solution after mixing. After 10 min, absorbance was measured at 540 nm using a Hewlett Packard (Agilent) 8453 UV-visible Spectroscopy. $NaNO_2$ solutions of 1-100 µM concentrations were used to prepare a standard nitrite curve of absorbance (nm) versus concentration (µM), and the NO released by DD-1 (quantitated as $NO_2^-$ release in µM) was calculated from the standard nitrite curve by extrapolation of the absorbance. Table 2 represents $NO_2^-$ release for compound DD-1.

TABLE 2

$NO_2^-$ release values for Compound DD-1.

| Incubation Time (Hours) | $NO_2^-$ release (µM) after 1 hour | $NO_2^-$ release (µM) after 16 hours |
|---|---|---|
| DD-1 | 9.61 | 5.35 |

<sup>a</sup>The $NO_2^-$ release (µM) was calculated from the standard $NaNO_2$ curve by extrapolating the absorbance (nm) of the test compounds against the concentration (µM) of $NaNO_2$.

Structural Studies of DD-1 in Complex with Deoxygenated Hb

The crystal structure of DD-1 was determined in complex with deoxy-Hb, to elucidate the structural basis of its allosteric activity. The crystallization experiment followed published procedure.[4] Briefly, 50 mg/mL of Hb and about 10 molar excess of DD-1 was mixed together. A small pellet of Nadithionite was added and the mixture evacuated for at least 1 h to make the deoxy-Hb solution. Subsequent crystallization of the compound-deoxy-Hb complex solutions in 10 mL test tubes was undertaken using low-salt precipitant of 0.2 M sodium acetate trihydrate, 0.1 M sodium cacodylate trihydrate pH 6.5 and 30% w/v PEG 8000. The entire crystallization experiment was performed in a glovebox under nitrogen atmosphere. Rectangular dark purple crystals grew to a size of about 0.2×0.3×0.4 mm in 3-5 days.

X-ray diffraction data was collected at 100K with a R-axis IV++ image-plate detector using CuKα x-rays (λ=1.54 Å) from Rigaku Micro-Max™-007 x-ray source equipped with varimax confocal optics (Rigaku, The Woodlands, Tex.) operating at 40 kv and 20 mA. Prior to use, the crystals were washed in a cryo-protectant solution containing mother liquor and glycerol and then flash frozen. The collected data sets were processed with MSC d*TREK software program and the CCP4 suite of programs. The structure was solved by molecular replacement using the deoxy-Hb structure in complex with RSR-13 (PDB ID: 1G9V) as the search model, and refined to an Rfactor/Rfree of 22.38%/26.38%.

Figure 5:
FIG. 5. Binding of a pair of DD-1 molecules (sticks) at the central water cavity of deoxy-Hb (in ribbons) in a symmetry-related fashion. Each molecule binds to three subunits.
Figure 6:
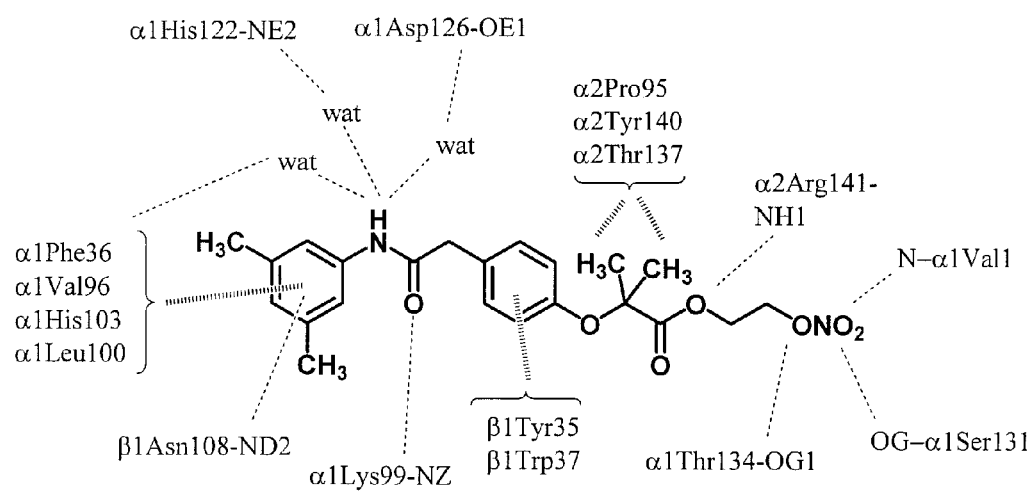
FIG. 6. Two-dimensional schematic of contacts between one of the DD-1 molecules and surrounding Hb residues. Narrow dashed lines indicate hydrogen bond/electrostatic interactions. Broad dashed lines indicate hydrophobic contacts.

The complex structure shows DD-1 bound in a symmetry-related manner at the middle of the central water cavity of deoxyHb (FIG. 5); similar to what was previously observed for RSR-13.[4] Each DD-1 molecule forms interactions with 3 subunits in a symmetry-related fashion —two α-subunits and 1 β-subunit that ties all three subunits together through hydrogen-bond and hydrophobic contacts with the protein residues as shown in FIG. 6. As previously noted for RSR-13,[4] these interactions stabilize the deoxy-Hb to shift the allosteric equilibrium to the T-state, decreasing the $O_2$ affinity of Hb.

Stability Studies of DD-1

The stability of nitrate esters was checked by performing UPLC-MS on a previously prepared stock solution of DD-1. A 100 µM stock solution was prepared in DMSO and stored for 3 months at −20° C. during which time it was exposed to at least 6 freeze-thaw cycles. It was observed that DD-1 was stable, suggesting no degradation.

REFERENCES

1. Benesch R, Benesch R E. The effect of organic phosphates from the human erythrocyte on the allosteric properties of hemoglobin. Biochem Biophys Res Commun 1967; 26:162-167.
2. Abraham D J, Wireko F C, Randad R S, Poyart C, Kister J, Bohn B, Liard J F, Kunert M P. Allosteric modifiers of hemoglobin: 2-[4-[[(3,5-disubstituted anilino)carbonyl]methyl]phenoxy]-2-methylpropionic acid derivatives that lower the oxygen affinity of hemoglobin in red cell suspensions, in whole blood, and in vivo in rats. Biochemistry 1992; 31:9141-9149.
3. Wireko F C, Kellogg G E, Abraham D J. Allosteric modifiers of hemoglobin. 2. Crystallographically determined binding sites and hydrophobic binding/interaction analysis of novel hemoglobin oxygen effectors. J Med Chem 1991; 34:758-767.
4. Safo M K, Moure C M, Burnett J C, Joshi G S, Abraham D J. High-resolution crystal structure of deoxy hemoglobin complexed with a potent allosteric effector. Protein Sci 2001; 10:951-957.
5. Safo M K, Boyiri T, Burnett J C, Danso-Danquah R, Moure C M, Joshi G S, Abraham D J. X-ray crystallographic analyses of symmetrical allosteric effectors of hemoglobin: compounds designed to link primary and secondary binding sites. Acta Crystallogr D Biol Crystallogr 2002; 58:634-644.
6. Pagel P S, Hettrick D A, Montgomery M W, Kersten J R, Warltier D C. RSR13, a synthetic allosteric modifier of hemoglobin, enhances recovery of stunned myocardium in dogs. Adv Exp Med Biol 1998; 454:527-531.
7. Scott C, Suh J, Stea B, Nabid A, Hackman J. Improved survival, quality of life, and quality-adjusted survival in breast cancer patients treated with efaproxiral (Efaproxyn) plus whole-brain radiation therapy for brain metastases. Am J Clin Oncol 2007; 30:580-587.
8. Stea B, Suh J H, Boyd A P, Cagnoni P J, Shaw E, REACH Study Group. Whole-brain radiotherapy with or without efaproxiral for the treatment of brain metastases: Determinants of response and its prognostic value for subsequent survival. Int J Radiat Oncol Biol Phys 2006; 64:1023-1030.
9. Suh J H, Stea B, Nabid A, Kresl J J, Fortin A, Mercier J P, Senzer N, Chang E L, Boyd A P, Cagnoni P J, Shaw E. Phase III study of efaproxiral as an adjunct to whole-brain radiation therapy for brain metastases. J Clin Oncol 2006; 24:106-114.
10. Cosby K, Partovi K S, Crawford J H, Patel R P, Reiter C D, Martyr S, Yang B K, Waclawiw M A, Zalos G, Xu X, Huang K T, Shields H, Kim-Shapiro D B, Schechter A N, Cannon R O, 3rd, Gladwin M T. Nitrite reduction to nitric oxide by deoxyhemoglobin vasodilates the human circulation. Nat Med 2003; 9:1498-1505.
11. Furchgott R F. Endothelium-derived relaxing factor: discovery, early studies, and identification as nitric oxide. Biosci Rep 1999; 19:235-251.
12. Furchgott R F, Jothianandan D. Endothelium-dependent and -independent vasodilation involving cyclic GMP: relaxation induced by nitric oxide, carbon monoxide and light. Blood Vessels 1991; 28:52-61.
13. Furchgott R F, Vanhoutte P M. Endothelium-derived relaxing and contracting factors. FASEB J 1989; 3:2007-2018.
14. Furchgott R F, Zawadzki J V. The obligatory role of endothelial cells in the relaxation of arterial smooth muscle by acetylcholine. Nature 1980; 288:373-376.

15. Maley J H, Lasker G F, Kadowitz P J. Nitric oxide and disorders of the erythrocyte: emerging roles and therapeutic targets. Cardiovasc Hematol Disord Drug Targets 2010; 10:284-291.
16. Rossaint R, Falke K J, Lopez F, Slama K, Pison U, Zapol W M. Inhaled nitric oxide for the adult respiratory distress syndrome. N Engl J Med 1993; 328:399-405.
17. Pison U, Lopez F A, Heidelmeyer C F, Rossaint R, Falke K J. Inhaled nitric oxide reverses hypoxic pulmonary vasoconstriction without impairing gas exchange. J Appl Physiol 1993; 74:1287-1292.
18. Roberts J D, Jr, Fineman J R, Morin F C, 3rd, Shaul P W, Rimar S, Schreiber M D, Polin R A, Zwass M S, Zayek M M, Gross I, Heymann M A, Zapol W M. Inhaled nitric oxide and persistent pulmonary hypertension of the newborn. The Inhaled Nitric Oxide Study Group. N Engl J Med 1997; 336:605-610.
19. Bloch K D, Ichinose F, Roberts J D, Jr, Zapol W M. Inhaled N O as a therapeutic agent. Cardiovasc Res 2007; 75:339-348.
20. Ichinose F, Roberts J D, Jr, Zapol W M. Inhaled nitric oxide: a selective pulmonary vasodilator: current uses and therapeutic potential. Circulation 2004; 109:3106-3111.
21. Roberts J D, Jr, Chiche J D, Weimann J, Steudel W, Zapol W M, Bloch K D. Nitric oxide inhalation decreases pulmonary artery remodeling in the injured lungs of rat pups. Circ Res 2000; 87:140-145.
22. Silverman T A, Weiskopf R B. Hemoglobin-based oxygen carriers: current status and future directions. Transfusion 2009; 49:2495-2515.
23. Silverman T A, Weiskopf R B, Planning Committee and the Speakers. Hemoglobin-based oxygen carriers: current status and future directions. Anesthesiology 2009; 111:946-963.
24. Weiskopf R B. Hemoglobin-based oxygen carriers: compassionate use and compassionate clinical trials. Anesth Analg 2010; 110:659-662.
25. Hess J R, MacDonald V W, Brinkley W W. Systemic and pulmonary hypertension after resuscitation with cell-free hemoglobin. J Appl Physiol 1993; 74:1769-1778.
26. Randad, R. S.; Mahran, M. A.; Mehanna, A. S.; Abraham, D. J. Allosteric modifiers of hemoglobin. 1. Design, synthesis, testing, and structure-allosteric activity relationship of novel hemoglobin oxygen affinity decreasing agents. J. Med. Chem. 1991, 34, 752-7.
27. Szabo C. Hydrogen sulphide and its therapeutic potential. Nat Rev Drug Discov 2007; 6:917-935.
28. Thatcher G R, Nicolescu A C, Bennett B M, Toader V. Nitrates and NO release: contemporary aspects in biological and medicinal chemistry. Free Radic Biol Med 2004; 37:1122-1143.
29. Sun, J.; Zhang, X.; Broderick, M.; Fein, H. Measurement of nitric oxide production in biological systems by using griess reaction assay. *Sensors* 2003, 3, 276-284.
30. Tsikas, D. Analysis of nitrite and nitrate in biological fluids by assays based on the griess reaction: Appraisal of the griess reaction in the L-arginine/nitric oxide area of research. *J. Chromatogr. B* 2007, 851, 51-70.
31. Molecular probes, Inc. Griess reagent kit for nitrite determination (G-7921). Product information, July 2003; 1-3.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound having the general formula:

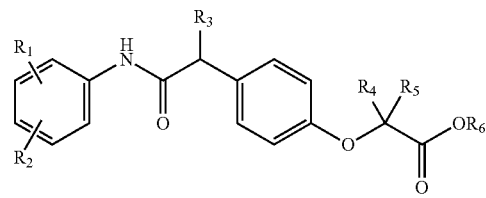

wherein
R1 and R2 are the same or different and are $CH_3$, Cl, H, $OCH_3$, or 5-carbon cyclic incorporating both R1 and R2;
R3 is H, OH, COOH, or $OC_2H_5$;
R4 and R5 are the same or different and are H, $CH_3$, cyclic incorporating both R4 and R5 and containing $CH_3$ substituents, $OCH_3$, $C_2H_5$, phenyl, or unsubstituted phenyl; and
R6 is a NO containing moiety selected from the group consisting of:

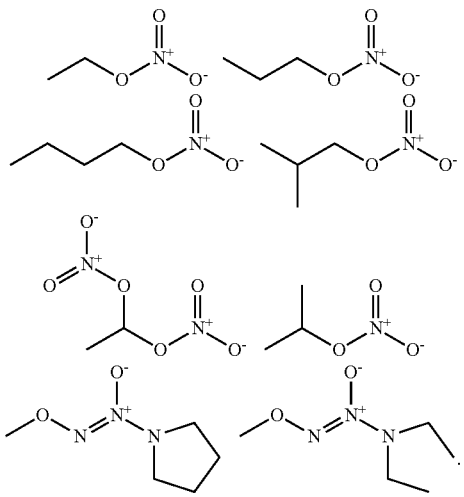

2. The compound of claim 1 having the formula:

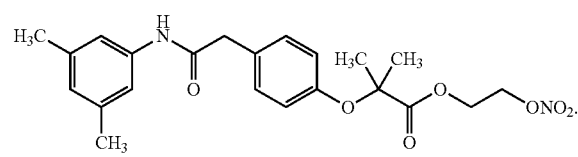

3. A composition, comprising:
one or more compounds as specified in claim 1; and
a carrier.
4. The composition of claim 3 wherein said carrier is a liquid, and wherein said one or more compounds are dissolved or distributed in said liquid.

5. The composition of claim 4 wherein said liquid is an aqueous liquid.

6. The composition of claim 4 wherein said liquid is an oil.

7. The composition of claim 3, wherein said carrier is a solid.

8. The composition of claim 3 wherein said carrier is a gas.

9. The composition of claim 8 wherein said gas is air.

* * * * *